United States Patent
Buchold et al.

(10) Patent No.: US 9,085,500 B2
(45) Date of Patent: Jul. 21, 2015

(54) METHOD FOR PRODUCING A PRODUCT CONTAINING $C_3H_6$ AND $C_2H_4$

(75) Inventors: Henning Buchold, Hanau (DE); Harald Koempel, Neu-Isenburg (DE); Sven Pohl, Frankfurt am Main (DE); Martin Rothaemel, Frankfurt am Main (DE); Ulrich Wagner, Biendorf (DE)

(73) Assignee: AIR LIQUIDE GLOBAL E&C SOLUTIONS GERMANY GMBH, Frankfurt am Main (DE)

( * ) Notice: Subject to any disclaimer, the term of this patent is extended or adjusted under 35 U.S.C. 154(b) by 456 days.

(21) Appl. No.: 13/139,008

(22) PCT Filed: Nov. 25, 2009

(86) PCT No.: PCT/EP2009/008395
§ 371 (c)(1),
(2), (4) Date: Aug. 16, 2011

(87) PCT Pub. No.: WO2010/066339
PCT Pub. Date: Jun. 17, 2010

(65) Prior Publication Data
US 2011/0288358 A1    Nov. 24, 2011

(30) Foreign Application Priority Data
Dec. 11, 2008 (DE) .......................... 10 2008 061 300

(51) Int. Cl.
*C07C 1/20* (2006.01)
(52) U.S. Cl.
CPC ............... *C07C 1/20* (2013.01); *C07C 2529/40* (2013.01)

(58) Field of Classification Search
USPC .................................................. 585/638–642
See application file for complete search history.

(56) References Cited

U.S. PATENT DOCUMENTS

| 4,396,789 A * | 8/1983 | Barrocas et al. ............... 585/639 |
| 4,542,252 A | 9/1985 | Graziani et al. |
| 6,441,262 B1 * | 8/2002 | Fung et al. .................... 585/640 |
| 2005/0107651 A1 | 5/2005 | Sher et al. |
| 2010/0063337 A1 | 3/2010 | Bach et al. |
| 2010/0268007 A1 | 10/2010 | Van Westrenen et al. |

FOREIGN PATENT DOCUMENTS

| DE | 257740 A3 | 6/1988 |
| DE | 19723363 A1 | 12/1998 |

(Continued)

OTHER PUBLICATIONS

European Patent Office, International Search Report in International Patent Application No. PCT/EP2009/008395 (Jun. 4, 2010).

*Primary Examiner* — In Suk Bullock
*Assistant Examiner* — Sharon Pregler
(74) *Attorney, Agent, or Firm* — Leydig, Voit & Mayer, Ltd.

(57) ABSTRACT

A process for producing a product containing C3H6 and C2H4 includes simultaneous conversion of MeOH and EtOH in an adiabatic sequentially operated reactor containing a plurality of reaction stages. Each of the plurality of reaction stages of the reactor is provided with a fixed bed of a form-selective catalyst. A gaseous feed stream including MeOH, DME and H2O is charged to at least a first of the reaction stages of the reactor with a temperature in a range of 300 to 600° C. at a pressure in a range of 0.1 to 20 bar[a]. EtOH is fed into at least, one of the reaction stages of the reactor.

20 Claims, 1 Drawing Sheet

(56) References Cited

FOREIGN PATENT DOCUMENTS

| | | |
|---|---|---|
| DE | 10027159 A1 | 12/2001 |
| DE | 10233975 A1 | 2/2004 |
| DE | 102006026103 A1 | 12/2007 |
| WO | WO 2005051872 A1 | 6/2005 |
| WO | WO 2009065870 A1 | 5/2009 |

* cited by examiner

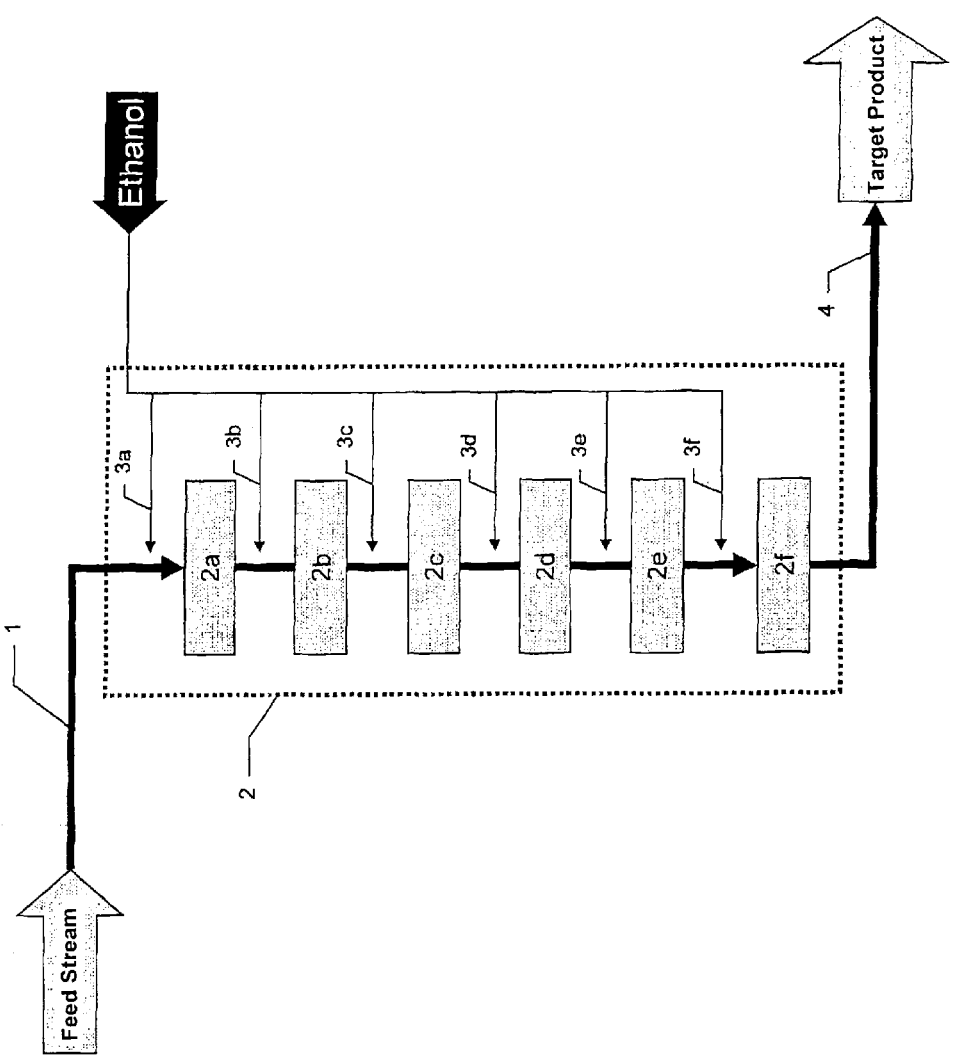

METHOD FOR PRODUCING A PRODUCT CONTAINING $C_3H_6$ AND $C_2H_4$

CROSS REFERENCE TO RELATED APPLICATIONS

This application is a U.S. National Phase application under 35 U.S.C. §371 of International Application No. PCT/EP2009/008395, filed on Nov. 25, 2009, and claims benefit to German Patent Application No. DE 10 2008 061 300.2, filed on Dec. 11, 2008. The International Application was published in German on Jun. 17, 2010 as WO 2010/066339 A1 under PCT Article 21 (2).

FIELD

The present invention relates to a process for producing a product containing $C_3H_6$ and $C_2H_4$.

BACKGROUND

In the petrochemical industry, the production of binary copolymers with a defined content of $C_3H_6$ and $C_2H_4$, typically 8% $C_2H_4$ and 92% $C_3H_6$, belongs to the most strongly growing product ranges. Correspondingly, processes for the targeted production of these mixtures of $C_2H_4$ and $C_3H_6$ are of particular interest. Furthermore, attempts are made to use other raw materials instead of petroleum as starting material for the production of olefins on a medium- and long-term basis.

DE 197 23 363 A1 describes a process for producing $C_2$- and $C_4$-olefins by reacting a vaporous reaction mixture containing MeOH and/or DME and $H_2O$ in a first reactor on a form-selective catalyst with temperatures of 280 to 570° C. at pressures of 0.1 to 1 bar[a], wherein a product mixture containing $C_2$- to $C_4$-olefins and gasoline hydrocarbons ($C_{5+}$) is withdrawn from the first reactor and a $C_{5+}$-stream rich in separated gasoline hydrocarbons is evaporated, mixed with steam, the weight ratio of $H_2O$ to hydrocarbons is adjusted to 0.5:1 to 3:1, and the mixture produced with a temperature of 380 to 700° C. is introduced into a second reactor containing a form-selective catalyst and a product mixture is withdrawn, whose added content of $C_3H_6$ and butene isomers is at least 50 wt-% of the olefin constituents of the feed mixture supplied to the second reactor.

DE 100 271 59 A1 describes the so-called MTPO process for producing $C_3H_6$ from MeOH, in which vaporous MeOH is reacted on a first catalyst to obtain a first vaporous mixture containing DME and on a form-selective zeolite catalyst arranged in at least two series-connected adiabatic shaft reactors a product mixture containing $C_3H_6$ is produced, wherein a first partial stream of the first vapor mixture containing DME together with $H_2O$ vapor is guided into the first shaft reactor, from which a first intermediate product mixture is withdrawn and charged to the second shaft reactor. To the second shaft reactor a second partial stream of the DME-containing first vapor mixture is supplied and from the last one of the series-connected shaft reactors a product mixture is withdrawn, from which a fraction rich in $C_3H_6$ is separated. The remaining partly gaseous residue containing $C_2H_4$ and $C_{4+}$-hydrocarbons is recirculated into one of the shaft reactors.

The subject-matter of US 2005/0107651 A1 is a process for producing a mixture containing MeOH and EtOH and for converting MeOH and EtOH to light olefins, wherein MeOH and EtOH with a weight ratio of 1 to 99% are supplied to a reaction zone in which MeOH and EtOH are reacted on a molecular sieve catalyst to obtain light olefins. In a similar process described WO 2005/051872 A1, the ratio of MeOH to EtOH in the feed stream is adjusted to 6 to 10.

DE 102 33 975 A1 deals with the production of $C_3H_6$ from MeOH, in which a vaporous mixture of MeOH, DME and $H_2O$ at operating temperatures of 250 to 460° C. is passed over a plurality of sequentially arranged reaction stages of an adiabatic reactor, which each are equipped with a form-selective zeolite catalyst with pentasil structure, and between the reaction stages cooling of the emerging reaction mixture takes place. After the last reaction stage, the cooled reaction mixture is separated into a gas phase and into a liquid phase chiefly containing water, and after a condensation the gas phase is separated into a gas phase containing hydrocarbons and into a liquid phase containing DME, MeOH and water, and thereafter $C_3H_6$ is removed from the gas phase. In an advantageous development of this process with regard to an improved heat guidance described in DE 10 2006 026 103 A1, a process stream containing DME and MeOH as well as $H_2O$ is cooled and separated into a liquid phase and into a gas phase, the gas and liquid phases are split up into a plurality of partial streams, whose number each corresponds to the number of spaces present between the reaction stages, and the individual gas phase partial stream is each charged to a nozzle tube with a liquid phase partial stream and the liquid phase is sprayed into the corresponding space by means of the gas phase.

DD 257 740 A3 relates to a process for producing $C_2$- to $C_4$-olefins by converting gases containing CO and $H_2$ to an alcohol mixture which contains MeOH and higher aliphatic alcohols in a mass ratio of MeOH to higher alcohols of 0.6 to 5.6, wherein the higher aliphatic alcohols are reacted on zeolitic catalysts with pentasil structure at temperatures of 250 to 600° C. and pressures of >100 kPa. By adjusting the indicated mass ratio between MeOH and higher alcohols, a heat compensation between exothermal MeOH conversion and endothermal dehydration of the higher alcohols largely is achieved during the conversion of the alcohol mixture on the conversion catalyst, which leads to an approximately thermoneutral reaction. The energy for the dehydration of the alcohol hence is provided by the MeOH conversion while simultaneously forming additional olefins. It is problematic, however, that with increasing retention time in the reactor the $C_2H_4$ formed from the fed EtOH is increasingly converted to other less valuable products such as olefins with more than four carbon atoms, paraffins, aromatics and/or naphthenes. In addition, there is the problem of the temperature control. When a product with a defined content of $C_3H_6$ and $C_2H_4$ is to be produced, an adiabatic temperature increase of 50 to 150° C. is obtained for the entire reaction. In a single-stage reactor the reaction accordingly passes through a wide temperature range. Since the selectivities for $C_3H_6$ and $C_2H_4$ increase with rising temperature, and on the other hand a maximum admissible temperature for the respective catalyst should not be exceeded, the reaction conditions become the more unfavorable the wider the temperature range passed through in the reactor becomes, with the consequence that the yield of target products is decreased.

SUMMARY

In an embodiment, the present invention provides a process for producing a product containing C3H6 and C2H4 including simultaneous conversion of MeOH and EtOH through a reaction in an adiabatic sequentially operated reactor containing a plurality of reaction stages. Each of the plurality of reaction stages of the reactor is provided with a fixed bed of a form-selective catalyst. A gaseous feed stream including MeOH, DME and H2O is charged to at least a first of the reaction stages of the reactor with a temperature in a range of 300 to 600° C. at a pressure in a range of 0.1 to 20 bar[a]. EtOH is fed into at least one of the reaction stages of the reactor.

BRIEF DESCRIPTION OF THE DRAWINGS

Exemplary embodiments are described in more detail below with reference to the drawing, in which:

FIG. 1 shows an embodiment of a process for producing $C_3H_6$ and $C_2H_4$ in a plurality of reaction stages.

DETAILED DESCRIPTION

The present invention relates to a process for producing a product containing $C_3H_6$ and $C_2H_4$ by simultaneously reacting MeOH and EtOH in an adiabatic, sequentially operated reactor containing a plurality of reaction stages, wherein each reaction stage is occupied with a fixed bed of a form-selective catalyst, in that a gaseous feed stream containing MeOH, DME, $H_2O$ and possibly one or more $C_2$-, $C_3$-, $C_4$-, $C_5$-, $C_6$-, $C_7$-, $C_8$-olefins and -paraffins is charged at least to the first reaction stage of the reactor with temperatures of 300 to 600° C. at pressures of 0.1 to 20 bar[a].

An aspect of the present invention is to design the process such that, with regard to the desired target product, the ratio of $C_2H_4$ to $C_3H_6$ is adjustable with sufficient accuracy. In an embodiment of the invention, EtOH is fed into at least one reaction stage of the reactor. By this measure, a better temperature control of the adiabatic conversion of the MeOH to hydrocarbons can be achieved, since the energy required for evaporation of the EtOH is removed from the reaction produced obtained during the exothermal conversion of the MeOH and the same is cooled thereby. The efficient temperature control of the chemical reactions taking place during the adiabatic conversion, which can be achieved by feeding EtOH, leads both to an increase in the yield of target products and to the saving of apparatuses, such as heat exchangers etc. Feeding EtOH into the multi-stage reactor in addition merely requires a charging means equipped with a flow control. Moreover, by additionally feeding EtOH, the ratio of $C_2H_4$ to $C_3H_6$ desired for the target product can be adjusted. Without the direct recooling of the reaction products produced during the conversion of MeOH, the temperature control of the conversion would require additional apparatuses, such as external or internal heat exchangers with cooling media as well as separators, external cooling means etc. and technical components. It is also advantageous that due to the endothermal conversion of EtOH to $C_2H_4$ the reaction heat of the exothermal reaction of the conversion of MeOH is distinctly reduced and as a result a particularly favorable temperature level is adjustable in the reactor.

With the short retention times existing in the reactor, the dehydration of EtOH to $C_2H_4$ takes place without any recognizable further reaction to undesired secondary products such as $C_{4+}$-olefins, paraffins, aromatics and/or naphthenes. As a result of the short retention times, which only are possible by supplying EtOH to a plurality of reaction stages, the conversion of EtOH and MeOH proceeds virtually independent of each other. Both of the above-described effects provide for a targeted product distribution of $C_2H_4$ and $C_3H_6$ due to a corresponding ratio of the quantities of EtOH and MeOH supplied to the reactor.

For the operation of the process it is advantageous when a zeolite with pentasil structure, preferably of the type ZSM-5 or MFI-Z, is used as the fixed-bed catalyst.

For carrying out the process, the reaction temperatures advantageously are adjusted to a range of 360 to 550° C., preferably 400 to 500° C., and the pressures are adjusted to a range of 0.5 to 5.0 bar[a], preferably 1.0 to 3.0 bar[a].

A preferred embodiment of the process of the invention is to be seen in that for producing the target product, an amount of 0.1 to 5.0 kg, preferably 0.3 to 3.0 kg, in particular 0.2 to 2.0 kg MeOH per kg of fixed-bed catalyst an hour is used and the total mass ratio of EtOH fed into the reactor to MeOH charged to the reactor (sum over all reaction stages) is 0.01 to 1.0 kg/kg, preferably 0.2 to 0.8 kg/kg, in particular 0.005 to 0.5 kg/kg.

Embodiments of the invention will be explained in detail below and by way of example:

Example 1

To illustrate the product distribution during the conversion of EtOH without addition of MeOH, 50 g of a zeolite catalyst are filled into an isothermal fixed-bed reactor, thereafter heating to a temperature of 450° C. is effected at a pressure of 1 bar[a], and an EtOH-water mixture is charged to the fixed-bed reactor. The hot reaction mixture produced is condensed and the gas-water phase or possibly present gasoline phases are analyzed separately. The analysis leads to the following results:
WHSV (EtOH) 1 (kg/kg·h)
WHSV ($H_2O$) 2 (kg/kg·h)
X (EtOH) 100(%)
Y ($C_2$=) 97 (mol C/mol C)
Y ($C_3$=) 1 (mol C/mol C)
Y (olefins) 99 (mol C/mol C)
Y (paraffins) 1 (mol C/mol C)
(WHSV~weight-hourly space velocity; X~conversion; Y~yield)
The results show that the conversion leads to $C_2H_4$ with a very high yield.

Example 2

With the same set-up and execution of the process as in Example 1, EtOH is converted in the presence of MeOH. For the simultaneous conversion of EtOH and MeOH, the selectivities of the conversion of EtOH only can be determined by accurately separating and calculating the conversion of MeOH with known selectivity distribution. The analysis leads to the following results:
WHSV (EtOH) 0.5 (kg/kg·h)
WHSV (MeOH) 0.5 (kg/kg·h)
WHSV ($H_2O$) 2 (kg/kg·h)
X (EtOH) 100(%)
Y ($C_2$=ex EtOH) 83 (mol C/mol C)
Y ($C_3$=) 10 (mol C/mol C)
Others 7 (mol C/mol C)
A comparative lineup of the analysis values reveals that the simultaneous conversion of EtOH and MeOH proceeds largely independent of each other.

From the results of the preceding Examples 1 and 2, the following embodiment illustrated in the drawing in FIG. 1 can be derived:

Via conduit (1), a gaseous feed stream substantially consisting of 40 wt-% MeOH and DME, 25 wt-% water and 35 wt-% hydrocarbons is introduced overhead into the reactor (2), in which six reaction stages (2a, 2b, 2c, 2d, 2e, 2f) vertically connected in series are incorporated, and supplied to the first reaction stage (2a) with a temperature of 460° C. at a pressure of 2.3 bar[a]. Via the conduits (3a, 3b, 3c, 3d, 3e, 3f) liquid EtOH is fed into the feed stream and into the intermediate product streams of the reaction stages (2b, 2c, 2d, 2e, 20 in a total amount of $EtOH_{total}$ to $MeOH_{total}$ of 1:10. At the outlet of the reactor (2) a product stream (target product) is withdrawn via conduit (4) and discharged for processing and separating the components.

If no liquid EtOH is introduced into the feed stream and into the product streams between the reaction stages, the following conversions (reference values) are obtained:

$C_3=\sim100\%; C_2=\sim100\%; C_{3=}/C_{2=}+C_3=\sim2.4\%.$

By adding liquid EtOH the conversions are improved as follows:

$C_3=\sim103\%; C_2=\sim490\%; C_{3=}/C_{2=}+C_3=\sim10.9\%.$

The additional formation of $C_3H_6$ partly results from the better temperature profile under the conditions of the addition of EtOH, whereby the inlet temperatures are raised by 2 to 5° C. per reaction stage, without the maximum temperature being exceeded at the end of each reaction stage.

With increasing number of reaction stages, the positive effect of the highly selective conversion of EtOH to $C_2H_4$ decreases, i.e. the further to the rear the feeding of EtOH is effected in the reactor equipped with a plurality of reaction stages, the better the target-oriented yield of the amount of EtOH fed into the reactor.

The process according to the invention thus provides for a targeted adjustment of the necessary product distribution of $C_2H_4$ and $C_3H_6$ for the production of polypropylene copolymers.

Another advantage achieved with embodiments of the invention consists in that for carrying out the process the use of pure EtOH (>99%) is omitted and technical EtOH (94%, rest water) can be utilized, as due to the positive effect of the multi-stage feeding of EtOH the water content not only does not disturb, but is also helpful for the progress of the entire reactions; for example, coking phenomena are suppressed more strongly and the adiabatic temperature increase is lowered.

The effect of the separately occurring conversion of the EtOH with simultaneously high yields of $C_2H_4$ and $C_3H_6$ practically can only be realized by the multi-stage feeding of the EtOH, as in this way at least the EtOH partial stream fed into the last reaction stage reacts to obtain the target products, in particular $C_2H_4$, with full yield. However, if the EtOH is dosed completely into a reaction stage, an increasing amount of undesired consecutive reactions take place from the initially formed $C_2H_4$.

While the invention has been particularly shown and described with reference to preferred embodiments thereof, it will be understood by those skilled in the art that various changes in form and details may be made therein without departing from the spirit and scope of the invention.

What is claimed is:

1. A process for producing a product containing propylene and ethylene by simultaneous conversion of methanol and ethanol through a reaction in an adiabatic sequentially operated reactor containing a plurality of reaction stages, the process comprising:

providing each of the plurality of reaction stages of the reactor with a fixed bed of a form-selective catalyst;

charging a gaseous feed stream comprising methanol, dimethyl ether, and $H_2O$ to at least a first of the reaction stages of the reactor with a temperature in a range of 300 to 600° C. at a pressure in a range of 0.1 to 5 bar[a];

feeding ethanol into more than one of the reaction stages of the reactor; and directing an effluent from a first reaction stage of the reaction stages to a next reaction stage of the reaction stages, wherein the more than one reaction stages comprise the final reaction stage.

2. The process recited in claim 1, wherein the gaseous feed stream further comprises a $C_2$-olefin, a $C_2$-paraffin, a $C_3$-olefin, a $C_3$-paraffin, a $C_4$-olefin, a $C_4$-paraffin, a $C_5$-olefin, a $C_5$-paraffin, a $C_6$-olefin, a $C_6$-paraffin, a $C_7$-olefin, a $C_7$-paraffin, a $C_8$-olefin, a $C_8$-paraffin, or a mixture of two or more of any of these.

3. The process recited in claim 1, wherein the fixed-bed catalyst includes zeolite of the pentasile type.

4. The process recited in claim 3, wherein the zeolite is of the type ZSM-5.

5. The process recited in claim 1, wherein the reaction is carried out at a temperature in a range of 360 to 550° C.

6. The process recited in claim 5, wherein the reaction is carried out at a temperature in a range of 400 to 500° C.

7. The process recited in claim 3, wherein the reaction is carried out at a temperature in a range of 360 to 550° C.

8. The process recited in claim 1, wherein the reaction is carried out at a pressure in a range 0.5 to 5.0 bar[a].

9. The process recited in claim 8, wherein the reaction is carried out at a pressure in a range of 1.0 to 3.0 bar[a].

10. The process recited in claim 3, wherein the reaction is carried out at a pressure in a range 0.5 to 5.0 bar[a].

11. The process recited in claim 5, wherein the reaction is carried out at a pressure in a range 0.5 to 5.0 bar[a].

12. The process recited in claim 1, wherein the methanol is charged to the reactor at a rate of 0.1 to 5.0 kg per kg of fixed-bed catalyst per hour and the total mass ratio of fed ethanol to charged methanol is 0.01 to 1.0 kg/kg.

13. The process recited in claim 12, wherein the methanol is charged to the reactor at a rate of 0.3 to 3.0 kg per kg of fixed-bed catalyst per hour.

14. The process recited in claim 13, wherein the methanol is charged to the reactor at a rate of 0.2 to 2.0 kg per kg of fixed-bed catalyst per hour.

15. The process recited in claim 12, wherein the ratio of the fed ethanol to the charged methanol is 0.02 to 0.8 kg/kg.

16. The process recited in claim 15, wherein the ratio of the fed ethanol to the charged methanol is 0.005 to 0.5 kg/kg.

17. The process recited in claim 3, wherein the methanol is charged to the reactor at a rate of 0.1 to 5.0 kg per kg of fixed-bed catalyst per hour and the total mass ratio of fed ethanol to charged methanol is 0.01 to 1.0 kg/kg.

18. The process recited in claim 5, wherein the methanol is charged to the reactor at a rate of 0.1 to 5.0 kg per kg of fixed-bed catalyst per hour and the total mass ratio of fed ethanol to charged methanol is 0.01 to 1.0 kg/kg.

19. The process recited in claim 8, wherein the methanol is charged to the reactor at a rate of 0.1 to 5.0 kg per kg of fixed-bed catalyst per hour and the total mass ratio of fed ethanol to charged methanol is 0.01 to 1.0 kg/kg.

20. The process recited in claim 1, wherein the ethanol in the feeding is added at each reaction stage of the reactor.

* * * * *